United States Patent [19]

Hill et al.

[11] Patent Number: Plant 7,526

[45] Date of Patent: May 21, 1991

[54] APPLE TREE HIDALA

[76] Inventors: John Hill; Sue Hill, both of "Hill Well" Orchard, Ormond Road, R.D. 5, Hastings, New Zealand

[21] Appl. No.: 344,110

[22] Filed: Apr. 26, 1989

[30] Foreign Application Priority Data

Apr. 27, 1988 [NZ] New Zealand ..... PV3/15/53

[51] Int. Cl.[5] ..... A01H 5/00

[52] U.S. Cl. ..... Plt./34

[58] Field of Search ..... Plt. 34

*Primary Examiner*—Howard J. Locker

*Attorney, Agent, or Firm*—Quarles & Brady

[57] ABSTRACT

The new and distinct variety of apple tree is a mutation of the Braeburn apple tree (an unpatented New Zealand variety). The fruit of the apple tree of this new variety has an attractive appearance characterized by its bright red color. The new variety has been name Hidala.

2 Drawing Sheets

SUMMARY OF THE INVENTION

The new variety which is a mutation of the Braeburn variety (an unpatented New Zealand variety) was found by us in February 1981. It was in the form of a single limb mutation growing in our orchard at Hastings, New Zealand. The new variety was distinguishable from Braeburn because of the red color of its fruit. We first performed asexual reproduction of the fruit in October 1983 when we grafted bud-wood onto MM106 root stock. The new variety has been named the Hidala variety. Asexual propagation shows that the unique combination of characteristics and distinctive color come true to form and are established and transmitted through succeeding propagations.

BRIEF DESCRIPTION OF THE DRAWING

The accompanying drawings show typical specimens of the foliage and fruit of the new variety as depicted in colors as nearly true as is reasonably possible to make the same in a color illustration of this character. In the drawings.

DETAILED DESCRIPTION OF THE DISCLOSURE

The following is a detailed description of our new variety with color terminology in accordance with the Munsell Notation except where general color terms of ordinary dictionary significance are clearly in turn intended by the context.

The specimens described were grown at our property in Hastings, New Zealand. The observations were made in the 1988/1989 season on trees which were four years old at the time and in the 1989/1990 season on trees which were five years old at the time.

The fruit ripened for eating toward mid-season. Specifically, the fruit ripened 14 days earlier than Granny Smith variety apples and 7 days later than Red Delicious.

Tree: Medium vigor; spreading habit; bearing, on spurs.

Trunk: Medium; smooth.

*Color.*—Grey 10 YR 4/2—Munsell Notation).

Branches: Medium thick; smooth; multi branching.

*Color.*—Grey (10 YR 5/1—Munsell Notation).

Lenticels: Less than average; small.

Leaves:

*Length.*—$3\frac{5}{8}$ inches.

*Width.*—$1\frac{7}{8}$ inches; medium size; upward pose; medium length/width ratio of blade; concave to straight shape in cross-section; crenate indentation of margin; medium glossiness of upper side; weak pubescence on lower side; long petiole length; small stipule size; early bud burst.

*Color.*—Green (7.5 GY 4/2—Munsell Notation).

Flowers: Early flowering; medium size; flat shape; margin of petals touching.

*Color of bud just before flower opens.*—Pink.

*Color of petal.*—Pink.

Fruit: Examined at peak maturity.

*Size.*—Large; axial diameter, 2 13/16 inches; transverse diameter $3\frac{1}{4}$ inches.

*Shape.*—Uniform; medium to long truncate; symmetrical in side view; no ribbing; weak crowning at distal end.

*Cavity.*—Medium depth; medium width.

*Basin.*—Medium to deep depth; medium to broad width; ribbing present.

Stem: Medium thickness (comparable to Cox's Orange Pippin); long length (comparable to Red Delicious).

Calyx: Closed.

*Calyx tube length.*—Short.

*Calyx tube width.*—Medium.

*Calyx tube shape.*—U or V shape.

Sepal:

*Length.*—Medium.

*Spacing.*—Just touching.

Eye:

*Size.*—Medium.

*Aperture.*—Half open.

Skin: Medium thickness; smooth.

*Bloom of skin.*—Absent.

*Greasiness of skin.*—Absent.

*Cracking tendency of skin.*—Absent.

*Background color.*—yellow/green (7.5 Y 7/5—Munsell Notation).

*Over-color.*—High percentage of over-color of skin; red (5R 4/6—Munsell Notation) streaked; weak russet about stem cavity.

Flesh: Juicy; firm; white (10 Y 8/3—Munsell Notation); weak browning of flesh (one hour after cutting stainless steel blade).

*Texture.*—Fine.

*Flavour.*—Medium sweetness; weak acidity.

*Quality.*—Excellent.

Core:

*Distinctness of core line in cross-section (medium through locules).*—Weak.

*Aperture of locules in cross-section.*—Open.

*Central cavity (in cross-section).*—Present.

Sinus: Closed.

Seeds: Medium sized; brown (approximately 5 YR 5/8—Munsell Notation).

Use: Market; dessert.

Keeping quality: Good.

Resistance to:

*Insects.*—Good.

*Diseases.*—Good.

Figure 1:
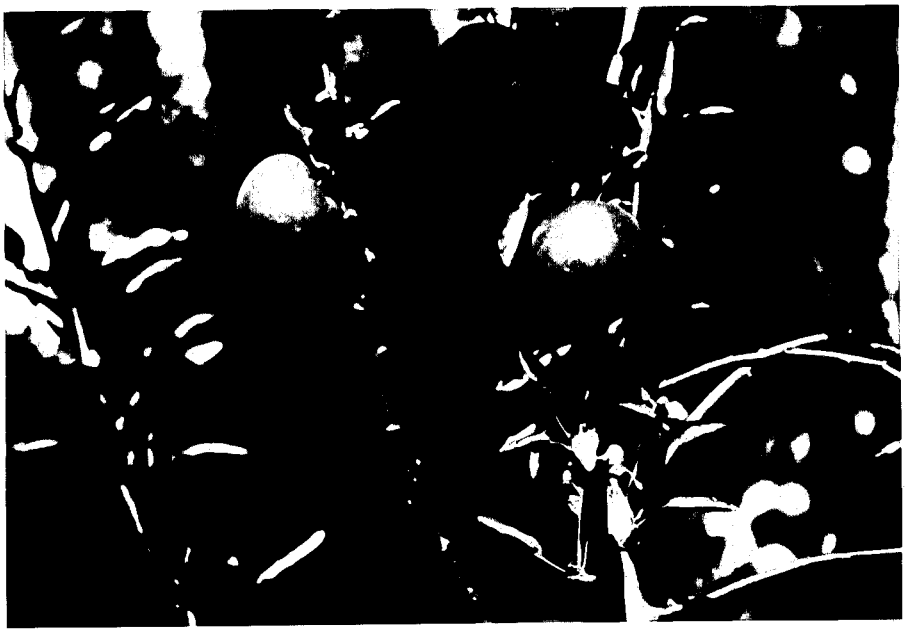
FIG. 1 is close-up view of five apples of the variety.
Figure 2:
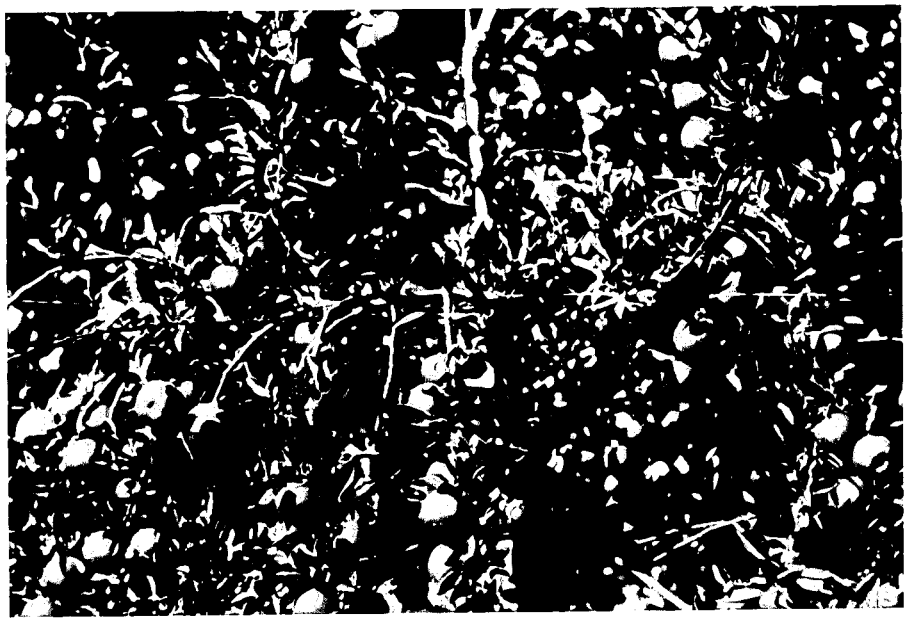
FIG. 2 is a more distant view showing details of the tree.
Figure 3:
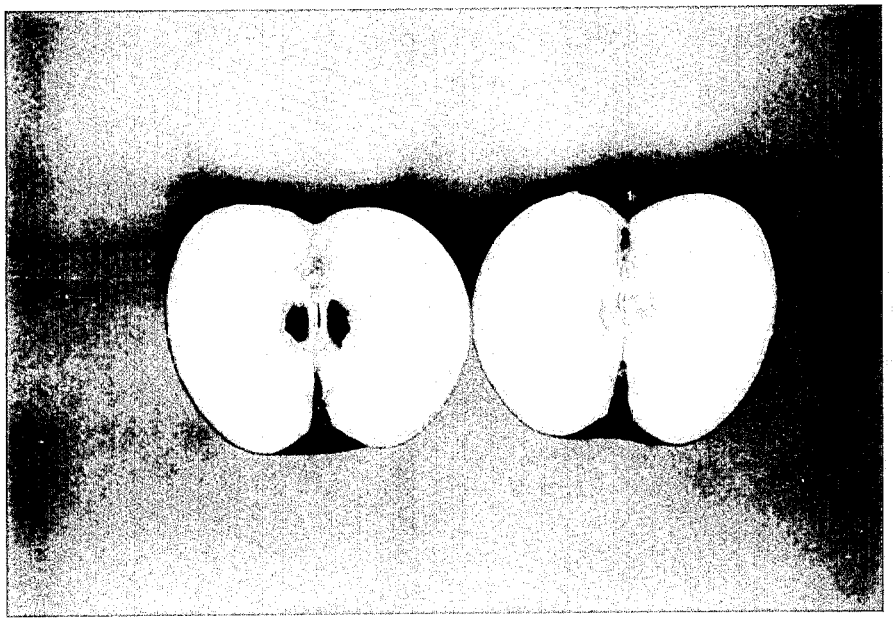
FIG. 3 is a sectional view of two halves of one fruit of the variety.
Figure 4:
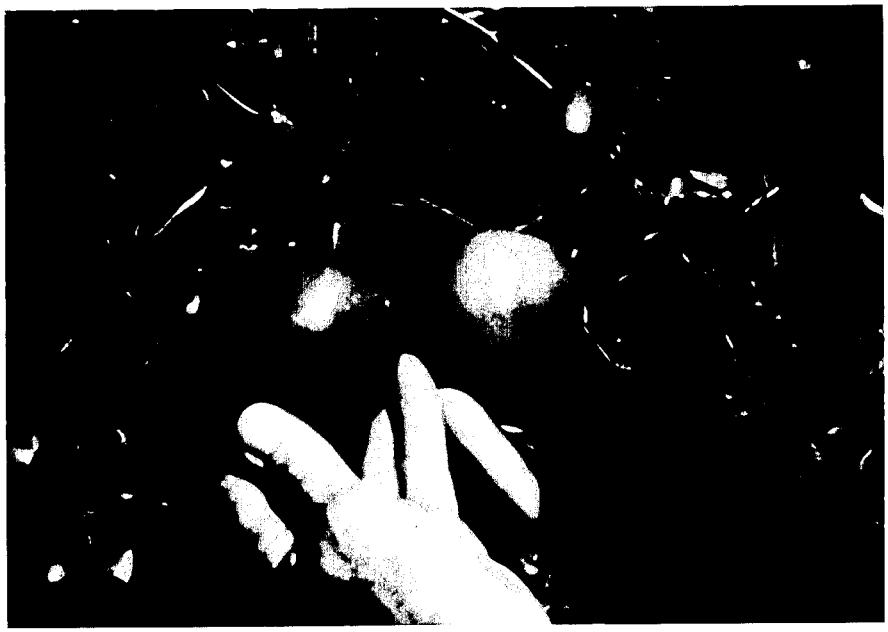
FIG. 4 is a side by side comparison of fruit of the new variety Hidala (on the left) with a fruit of prior variety Braeburn (on the right).

The main distinguishing characteristic between the Hidala variety and the Braeburn variety has to do with the color of the fruit. By Munsell Notation, the Braeburn variety fruit has a background of 10 Y 7/6 with a red over color of 7.5 R 4/6. The Braeburn fruit skin color is thus a bright fleck orange red expressed as a positive stripe over an over washed color of blush over 40 to 50% of the fruit surface area. The Hidala skin color is 50 to 70% block red overlaid by an even darker fleck. As can be seen by referring to FIG. 4, the Hidala apple has an overall more reddish appearance compared to the Braeburn apple which exhibits a much greater proportion of the background color.

Hidala has been observed to have less vigor and vegetation than Braeburn trees growing in similar properties. Hidala and Braeburn bloom at the same time.

The apples have been picked from Hidala at the same time or earlier than the picking of Braeburn apples which in New Zealand is in the range of from 19 March to 21 April. Like Braeburn, the Hidala tree tends to be biennial bearing.

We claim:

1. A new and distinct variety of apple tree which is a mutation of the Braeburn variety (an unpatented New Zealand variety) substantially as shown and described, characterized by the bright red color of the fruit which extends substantially over the entire surface of the fruit.

* * * * *